(12) United States Patent
Kwak et al.

(10) Patent No.: US 10,188,875 B2
(45) Date of Patent: Jan. 29, 2019

(54) TUMOR SURFACE DOSE ENHANCING RADIOTHERAPY APPARATUS USING MAGNETIC FIELD

(71) Applicant: THE ASAN FOUNDATION, Seoul (KR)

(72) Inventors: Jung Won Kwak, Namyangju-si (KR); Nurihyun Jung, Daegu (KR); Byung Chul Cho, Anyang-si (KR); Seung Do Ahn, Seoul (KR); Sang Wook Lee, Seoul (KR); Jae Beom Bae, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 151 days.

(21) Appl. No.: 15/293,293

(22) Filed: Oct. 14, 2016

(65) Prior Publication Data
US 2017/0106214 A1 Apr. 20, 2017

(30) Foreign Application Priority Data
Oct. 16, 2015 (KR) .................. 10-2015-0144652

(51) Int. Cl.
*A61N 5/10* (2006.01)

(52) U.S. Cl.
CPC .......... *A61N 5/1065* (2013.01); *A61N 5/1071* (2013.01); *A61N 5/1077* (2013.01)

(58) Field of Classification Search
None
See application file for complete search history.

(56) References Cited

U.S. PATENT DOCUMENTS 5,986,274 A * 11/1999 Akiyama ............ A61N 5/10
250/492.1

FOREIGN PATENT DOCUMENTS

KR 10-1378447 B1 3/2014

OTHER PUBLICATIONS

Radiation Oncology Journal, Trilateral Symposium & The 32nd Annual Meeting of KOSRO, Oct. 16-17, 2014, 66 pages, vol. 32, Suppl. 2, The Korean Society for Radiation Oncology, Seoul, Korea.

* cited by examiner

*Primary Examiner* — Hoon Song
(74) *Attorney, Agent, or Firm* — Studebaker & Brackett PC

(57) ABSTRACT

Disclosed is a tumor surface dose enhancing radiotherapy apparatus using a magnetic field, including a radiation beam generating unit that irradiates a radiation beam towards a tumor of a patient, a magnetic field generating unit that forms a magnetic field that is parallel to the radiation beam between the radiation beam generating unit and the tumor of the patient, and a control unit that controls a surface dose of the tumor by adjusting an intensity and an effective area of the magnetic field of the magnetic field generating unit.

4 Claims, 6 Drawing Sheets
(5 of 6 Drawing Sheet(s) Filed in Color)

TUMOR SURFACE DOSE ENHANCING RADIOTHERAPY APPARATUS USING MAGNETIC FIELD

CROSS-REFERENCE TO RELATED APPLICATIONS

A claim for priority under 35 U.S.C. § 119 is made to Korean Patent Application No. 10-2015-0144652 filed Oct. 16, 2015, in the Korean Intellectual Property Office, the entire contents of which are hereby incorporated by reference.

BACKGROUND

Embodiments of the inventive concept described herein relate to a radiotherapy apparatus that enhances a surface dose of a tumor that is a target object, by using a magnetic field, and more particularly to a radiotherapy apparatus that enhances a surface dose of a tumor by applying a magnetic field in a direction that is parallel to a radiation beam and thus concentrating scattering charged particles that are generated due to the heterogeneous density of human body tissues included within the beam locus of the radiation without diverging the charged particles in order to prevent the charged particles from scattering to outside of the tumor surface that is a treatment target, thereby improving a radiotherapy effect.

The radiotherapy apparatus is medical equipment that uses radiation in treatment of diseases, and is widely used to retard, stop, or even destruct growth of malignant tumors, such as cancers, by using ionizing radiation, including photon, electron or charged particle beam.

Meanwhile, because the charged particles that have scattered in a beam locus of the radiation diverge as their free flight distances increase in an interior (or a low density space) of an organ, such as a lung, an oral cavity, or an airway, there is 'Build-up phenomenon' in which absorbed radiation dose at a surface of a tumor is decreased.

Accordingly, because a surface of a tumor that is adjacent to a low density area gets lower radiation dose, a larger amount of radiation need to be irradiated to compensate lower radiation dose at the tumor surface, and consequently, normal tissues nearby the tumor get high dose of radiation.

In particular, the lung tumor requires a larger amount of radiation to be irradiated so that a dose that is necessary for the tumor destruction is delivered to the surface of the tumor because the tumor is surrounded by low density materials (normal lung tissues), and as a result, the treatment effect decreases due to the side effect of the radiation as the radiation dose delivered to the normal lung tissues increase.

Accordingly, if a method through which charged particles that are apt to diverge may be concentrated on a surface of a tumor is developed, an additional radiation dose for compensating for divergence of the charged particles from the tumor surface to surrounding normal tissues can be eliminated.

Accordingly, a radiotherapy apparatus that enhances a surface dose by concentrating the charged particles on a tumor by applying a magnetic field that is parallel to the direction of a beam of a radiation to a portion at which scattering charged particles diverge has been developed.

SUMMARY

Embodiments of the inventive concept provide a tumor surface dose enhancing radiotherapy apparatus using a magnetic field, by which the complementation of the lack of a dose on the tumor surface, which is caused when scattering charged particles diverge at a portion having low density and propagation of the radiation dose to the normal tissues, and a side effect of the radiation beam can be reduced and a treatment effect can be improved by securing a dose of the tumor surface.

In accordance with an aspect of the inventive concept, there is provided a tumor surface dose enhancing radiotherapy apparatus using a magnetic field, including a radiation beam generating unit that irradiates a radiation beam towards a tumor of a patient, a magnetic field generating unit that forms a magnetic field that is parallel to the radiation beam between the radiation beam generating unit and the tumor of the patient, and a control unit that controls a surface dose of the tumor by adjusting an intensity and an effective area of the magnetic field of the magnetic field generating unit.

Here, the magnetic field generating unit may form a homogenous or heterogeneous magnetic area at a whole part or a portion of a beam locus of the radiation.

Further, the control unit may include a calculation unit that calculates the surface dose of the tumor that is delivered to the tumor of the patient via the magnetic field area.

The calculation unit may calculate a surface dose of a tumor that is delivered to a tumor of the patient by using Equation 1.

$$D(x,y,z) = \iiint TERMA(x',y',z') \times Kernel(x,x',y,y',z,z')dx'dy'dz' \qquad <\text{Equation 1}>$$

Here, D(x, y, z) denotes a surface dose value of a tumor by which a radiation beam is delivered to a tumor of the patient, TERMA (x', y', z') denotes total energy of a incident radiation beam that is damped in an infinitesimal volume dx'dy'dz', and Kernel (x, x', y, y', z, z') denotes a ratio of a dose that is absorbed at the specific location (x, y, z) of unit energy that is damped at the infinitesimal volume dx'dy'dz'. Then, a kernel that considers a magnetic field formed by the magnetic field generating unit is used.

Further, the magnetic field generating unit may include electromagnets, permanent magnets, or combination type magnets thereof, and may function to maintain a direction of the magnetic field in parallel to a direction of a beam of the radiation.

The magnetic field generating unit may be rotated round the patient or may be fixedly or movably arranged along a circumference of the patient. In the fixed magnetic field generating unit, a patient fixing table may be movable such that a radiation beam may be irradiated to a target object in various directions while the location of the patient is changed.

BRIEF DESCRIPTION OF THE FIGURES

The patent or application file contains at least one drawing executed in color. Copies of this patent or patent application publication with color drawing(s) will be provided by the Office upon request and payment of the necessary fee.

The above and other objects and features will become apparent from the following description with reference to the following figures, wherein like reference numerals refer to like parts throughout the various figures unless otherwise specified, and wherein.

DETAILED DESCRIPTION

Hereinafter, the inventive concept will be described in detail with reference to the accompanying drawings.

Figure 1:
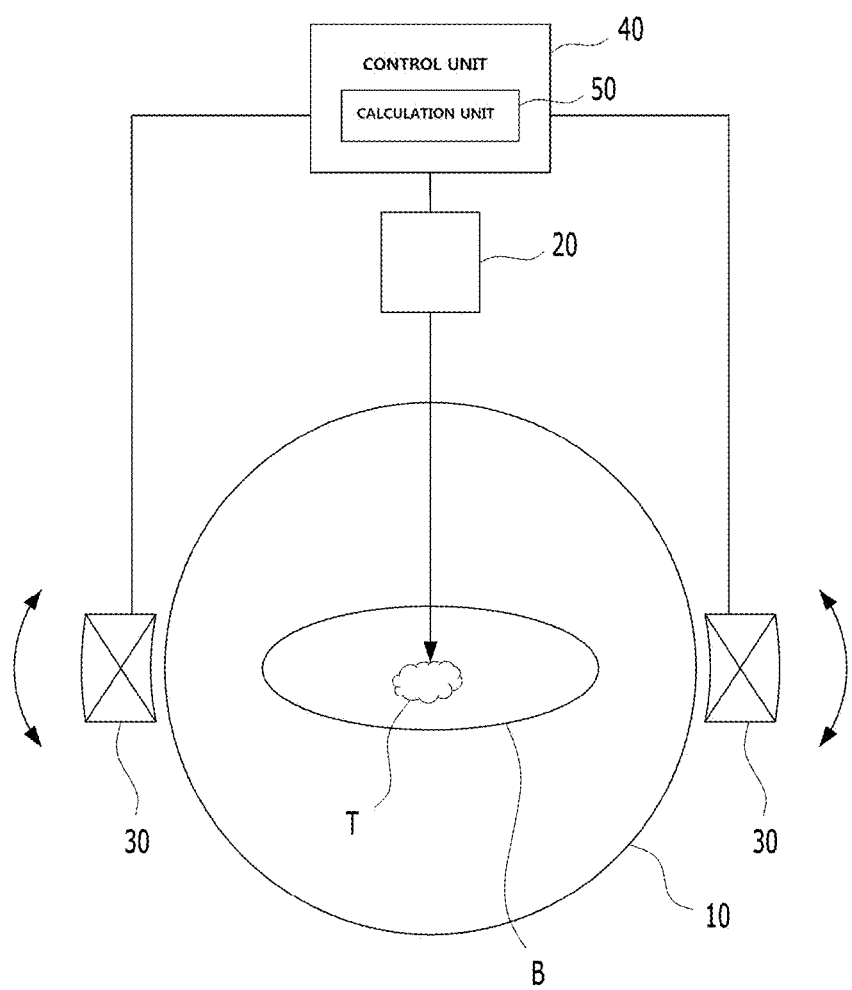
FIG. 1 is a schematic diagram of a tumor surface dose enhancing radiotherapy apparatus using a magnetic field according to an embodiment of the inventive concept.

FIG. 1 is a schematic diagram of a tumor surface dose enhancing radiotherapy apparatus using a magnetic field according to an embodiment of the inventive concept.

As illustrated in the drawing, the tumor surface dose enhancing radiotherapy apparatus using a magnetic field according to the embodiment of the inventive concept may include a radiation beam generating unit 20, a magnetic field generating unit 30, and a control unit 40.

The radiation beam generating unit 20 is mounted in a structure that is arranged on the outer side of a bore 10 having a hollow shape, and irradiates radiation beams towards a portion of a tumor T of a patient B situated in the bore 10.

Here, the radiation beam generating unit 20 may be a linear accelerator (LINAC) that generates MV X-rays, but also corresponds to all radiation beams (electrons, protons, neutrons, baryons, and the like) that are charged particles themselves or are related to the charged particles. In particular, the radiation beam generating unit 20 delivers kinetic energy to secondary electrons through a reaction due to Compton effect on a surface of a material that is exposed to radiation due to the characteristics of X-ray beams in a generated MV area, and delivers the radiation dose to the interior of the human body by using electrons.

The magnetic field generating unit 30 may be mounted to another structure on the outside of the bore 10, and may form a magnetic field area in the interior of the body of the patient B and all areas related to a locus of a beam. The magnetic field generating units 30 may be arranged opposite to each other while the bore 10 is interposed between, and may form a magnetic field that is parallel to a radiation beam that is situated between the radiation beam generating unit 20 and the tumor T of the patient B and is radiated towards the tumor T.

Figure 2:
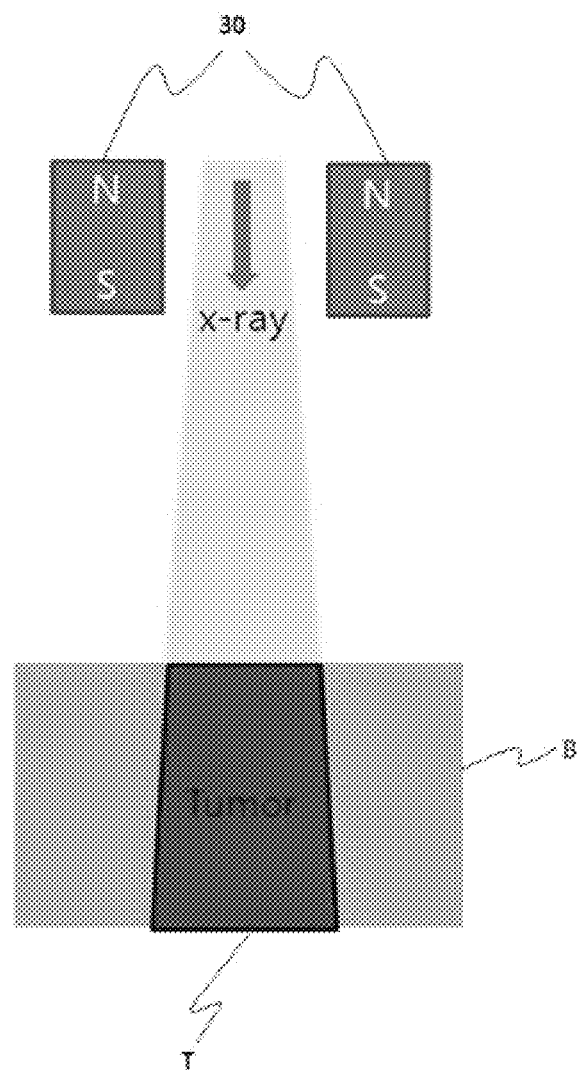
FIG. 2 is a diagram illustrating the concept of the tumor surface dose enhancing radiotherapy apparatus using a magnetic field of FIG. 1.

Meanwhile, as an embodiment, as illustrated in FIG. 2, in the magnetic field generating unit 30, a plurality of magnets are arranged around the radiation beam to be opposite to each other such that the magnets of the same polarities face each other so that a magnetic field that is parallel to the radiation beam irradiated to the tumor T of the patient B is generated, and the magnets may have a specific length.

Figure 3:
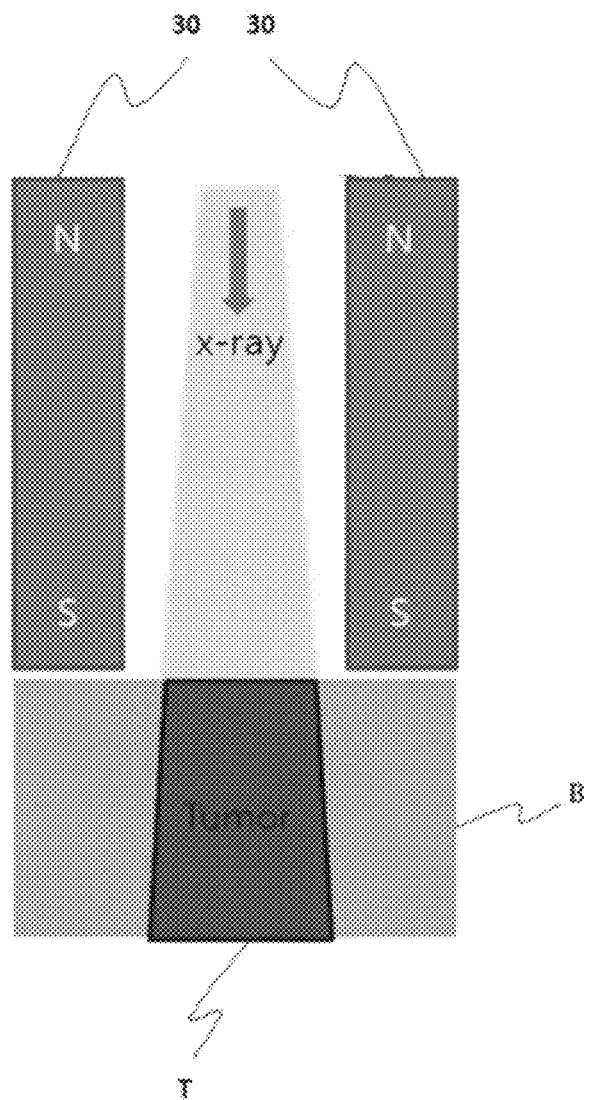
FIG. 3 is a diagram illustrating arrangement of a magnetic field generating unit according to another embodiment of the inventive concept.

Meanwhile, as another embodiment, as illustrated in FIG. 3, in the magnetic field generating unit 30, a plurality of magnets are arranged around the radiation beam to be opposite to each other such that the magnets of the same polarities face each other so that a magnetic field that is parallel to the radiation beam irradiated to the tumor T of the patient B is generated, and the magnets may extend to a surface of the tumor T.

As illustrated in FIGS. 2 and 3, when the plurality of magnets of the magnetic field generating unit 30 are arranged opposite to each other around the radiation beam such that the magnets of the same polarities face each other, the magnets may have various lengths.

Figure 4:
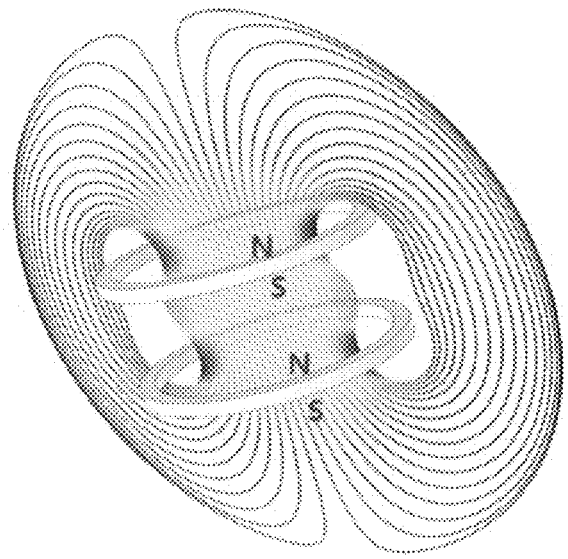
FIG. 4 is a diagram illustrating arrangement of a magnetic field generating unit and formation of a magnetic field according to another embodiment of the inventive concept.

As another embodiment, as illustrated in FIG. 4, in the magnetic field generating unit 30, a plurality of magnets, on which coils are wound, may be arranged at an interval along an irradiation direction of a radiation beam, which is irradiated to a tumor T of the patient B while surrounding a circumference of the radiation beam such that the magnets of the opposite polarities face each other so that a magnetic field that is parallel to the radiation beam is generated in a form of a Helmholtz coil, and FIG. 4 is a diagram illustrating formation of a magnetic field based on the arrangement.

Figure 5:
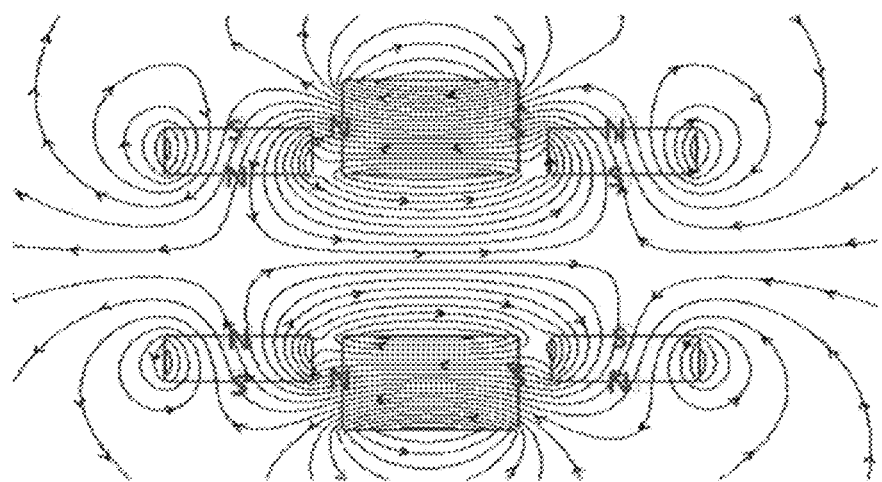
FIG. 5 is a diagram illustrating arrangement of a magnetic field generating unit and formation of a magnetic field according to another embodiment of the inventive concept.

Further, as another embodiment, as illustrated in FIG. 5, the magnetic field generating unit 30 may be configured such that a plurality of main magnets are arranged around a circumference of a radiation beam, which is irradiated to a tumor T of the patient B to be opposite to each other such that the magnets having the same polarities face each other so that a magnetic field that is parallel to the radiation beam is generated based on Ampere's right-handed screw rule, an auxiliary magnet may be arranged on one side of each of the main magnets such that a magnet is formed on the outside of the irradiation direction of the radiation beam, and another auxiliary magnet may be arranged on an opposite side of each of the main magnets such that a magnetic field is formed on the inside of the irradiation direction of the radiation beam, and FIG. 5 is a diagram illustrating formation of a magnetic field based on the arrangement.

Because the magnets of the magnetic field generating unit 30 are arranged as illustrated in the embodiments, emitted electrons are helically moved by a magnetic field that is parallel to a radiation beam while passing through the magnetic field area and move together with the radiation beam while being neither deflected nor dispersed.

Here, in the magnetic field generating unit 30, it is effective to form a magnetic field area in one area of the interior of the body of the patient B between the radiation beam generating unit 20 and a tumor T of the patient B, more preferably, in a body cavity or a portion (a lung) having low density. Further, the magnetic field generating unit 30 may form a homogeneous or heterogeneous magnetic field area in the whole part or a portion of the beam locus of the radiation. Further, the magnetic field generating unit 30 may include an electromagnet, a permanent magnet, or a combination type magnet.

Meanwhile, the present embodiment illustrates that the magnetic field generating unit 30 is configured that a pair of magnets are rotated along an outer circumference of the bore 10, for example, around the patient B situated in the bore 10 to improve a degree of freedom of a direction of a magnetic field, the inventive concept is not limited thereto, but the magnetic field generating unit 30 may be configured such that a plurality of magnets are fixedly arranged along an outer circumference of the bore 10, for example, around the patient B so that a magnetic field area is formed by magnets that are selected from the plurality of magnets under the control of the control unit 40.

The control unit 40 controls a surface dose of a tumor that is delivered from the radiation beam generating unit 20 to the tumor T of the patient B by adjusting the intensity and the effective area of the magnetic field of the magnetic field generating unit 30, thereby concentrating the surface dose of the tumor on the tumor T of the patient B and thus enhancing the surface dose of the tumor. The control unit 40 may adjust the intensity and the effective area of the magnetic field while rotating the magnetic field generating unit 30 to a desired location along the circumference of the patient B.

Further, the control unit 40 controls an operation of the radiation beam generating unit 20.

Meanwhile, the control unit 40 further includes a calculation unit 50 that calculates a surface dose of a tumor that is delivered to a tumor T of the patient B via a magnetic field area.

The calculation unit 50 calculates a surface dose of a tumor that is delivered to the tumor T of the patient B by using Equation 1.

$$D(x,y,z) = \iiint TERMA(x',y',z') \times Kernel(x,x',y,y',z,z') dx'dy'dz' \quad \text{<Equation 1>}$$

Here, D(x, y, z) denotes a surface dose value of a tumor that is absorbed at a specific location (x, y, z), TERMA (x', y', z') denotes total energy of a incident radiation beam that is damped in an infinitesimal volume dx'dy'dz', and Kernel (x, x', y, y', z, z') denotes a ratio of a dose that is absorbed at the specific location (x, y, z) of unit energy that is damped at the infinitesimal volume dx'dy'dz'. Then, a kernel that considers a magnetic field formed by the magnetic field generating unit 30 is used.

Accordingly, if the TERMA value and the Kernel value are convoluted for the entire volume, a surface dose value of a tumor that is absorbed at the specific location (x, y, z) may be calculated.

Meanwhile, because the TERMA value represents total damped energy of the X ray that does not have a charge.

Further, because the Kernel value represents spatial distribution of doses mainly due to the electrons generated in the damping process, it is absolutely influenced by a magnetic field. In general, the Kernel value is obtained through a simulation and a new Kernel value is obtained by implementing a spatially constant magnetic field in a simulation program, and accordingly, a Kernel deformation map is constituted as follows. The Kernel deformation map is modeled and applied as in Equation 2.

$$Kernel_{new}(B,x,x',y,y',z,z') = Deform\_map(Kernel(x,x',y,y',z,z'),B) \quad \text{<Equation 2>}$$

Accordingly, the calculation unit 50 calculates the intensity, the direction, and the magnitude of a magnetic field for optimizing distribution of a radiation dose.

Meanwhile, as another embodiment, the calculation unit 50 may calculate the radiation dose of a tumor under magnetic fields through a full Monte Carlo simulation method.

That is, a surface dose value of a tumor that is absorbed at a specific location may be calculated constituting histories by using a toolkit that may simulate a magnetic field and a stochastic Monte Carlo method for respective particles, and calculating a total dose distribution in addition to a spatial influence on the doses of the histories.

Accordingly, the control unit 40 may plan a surface dose of a tumor, and may calculate the distribution and intensity of the magnetic field through the calculation unit 50.

Hereinafter, a process of performing radiotherapy on a tumor T of the patient B through a tumor surface dose enhancing radiotherapy apparatus using a magnetic field according to the inventive concept will be described based on the configuration.

Figure 6:
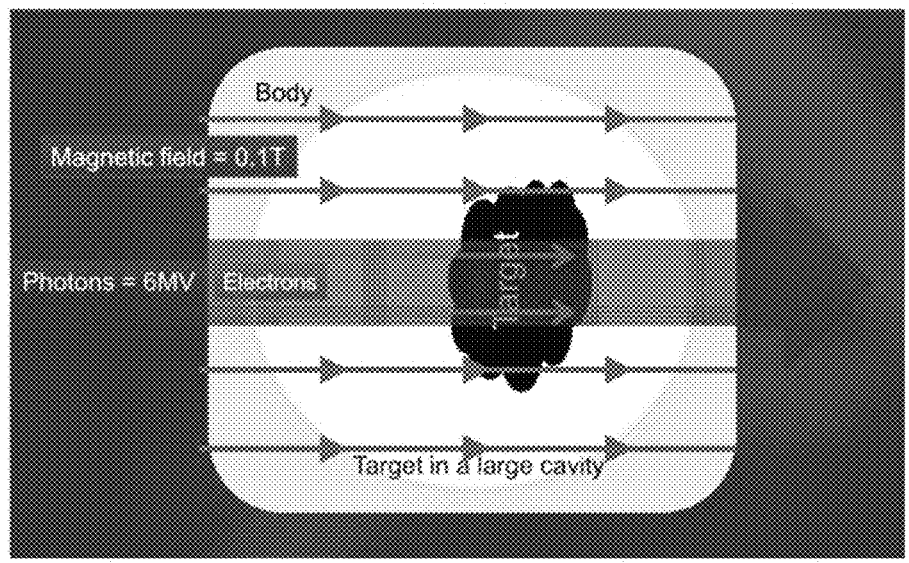
FIG. 6 is a view for explaining an operational relationship between electrons and a magnetic field based on irradiation of radiation beams in the tumor surface dose enhancing radiotherapy apparatus using a magnetic field according to the inventive concept.

Prior to the description thereof, as an embodiment, as illustrated in FIG. 6, a process of enhancing a treatment of a surface of a tumor T when a radiation beam is irradiated to the tumor T from the left side to the right side of FIG. 6, a magnetic field is applied in a direction that is parallel to the radiation beam, and an organ (a lung, an oral cavity, or an airway) having a low internal density is arranged between the radiation beam generating unit 20 and the tumor.

First, while the patient B who has a tumor T that is to be treated is lying in the bore 10, the magnetic field generating unit 30 is operated under the control of the control unit 40 such that a magnetic field area is formed in the interior of the body of the patient B.

Next, under the control of the control unit 40, the radiation beam generating unit 20 is operated such that the radiation beam is irradiated towards the tumor T of the patient B.

Then, while the radiation beam generated by the radiation beam generating unit 20 passes through the interior of the body of the patient B, charged particles, that is, electrons are emitted. The emitted electrons function to deliver high energy of the radiation beam. Here, the magnetic field area may be formed at the same time when the radiation beam is irradiated.

Meanwhile, the emitted electrons pass through the magnetic field area formed in the interior of the human body through the magnetic field unit 30, are helically moved by the magnetic field that is parallel to the beam of the radiation while passing through the magnetic field area, and are moved to the tumor T that is a target while being neither deflected nor dispersed.

In more detail, the emitted electrons are moved along the irradiation direction of the beam of the radiation while being spirally moved by a force due to a magnetic field and are moved to the tumor T that is the target.

That is, as illustrated in FIG. 6, a radiation beam is irradiated from the radiation beam generating unit 20 situated on the left side to the tumor T situated on the right side and a magnetic field is applied in parallel to the irradiation direction of the beam of the radiation, electrons are emitted while photons generated by the radiation beam generating unit 20 situated on the left side passes through the interior of the body of the patient B, and the emitted electrons are moved together with the photons to the tumor T that is a target via a magnetic field area along the irradiation direction of the radiation beam.

Then, While the emitted electrons pass through the magnetic field area, the electrons that passed through the magnetic field area are moved together with the beam of the radiation by adjusting the intensity and the effective area of the magnetic field of the magnetic field generating unit 30 under the control of the control unit 40 based on the calculation of the calculation unit 50 so that the electrons of an amount corresponding to a suitable radiation dose are delivered to the target T that is the target via a low density space such that a proper surface dose of a tumor is concentrated and irradiated on a surface of the tumor T.

Further, a maximum amount of electrons emitted by the radiation beam are delivered to the surface of the tumor T while the electrons being neither deflected nor dispersed to an empty space area in the interior of the organ as illustrated in FIG. 6, by adjusting the intensity and the effective area of the magnetic field in the magnetic field generating unit 30 under the control of the control unit 40 through the calculation of the calculation unit 50.

Accordingly, a radiation dose that is delivered to a surface of the tumor T that is a treatment target may be enhanced by preventing divergence of scattering charged particles of the radiation beam and concentrating the scattering charged particles, so that the effect of the radiotherapy may be improved. Further, damage to surrounding normal tissues due to additional use of radiation beams and divergence of scattering charged particles may be reduced and a side effect of the radiation may be reduced.

Hereinafter, a test result of the tumor surface dose enhancing radiotherapy apparatus using a magnetic field according to the inventive concept will be described.

Figure 7:
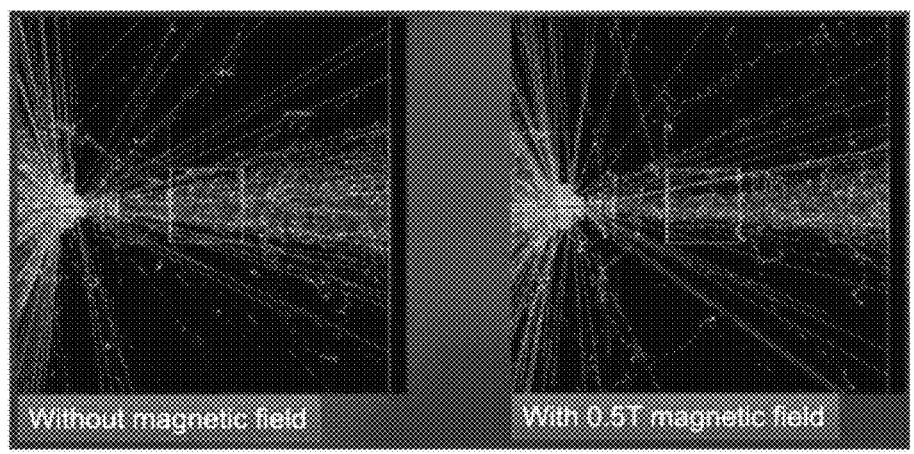
FIG. 7 is a view illustrating a simulation of electrons that are generated when radiation beams are irradiated based on existence of a magnetic field area as an example.

FIG. 7 is a view illustrating a simulation of electrons that are generated when radiation beams are irradiated based on existence of a magnetic field area as an example.

The left side of FIG. 7 illustrates a result of a simulation of flows of electrons when an X ray of 6 MV is irradiated to an area in which a magnetic field is not formed, and the right side of FIG. 7 illustrates a result of a simulation of flows of electrons when an X ray of 6 MV is applied to a magnetic field area of 0.5 T (Tesla).

As illustrated in FIG. 7, as the intensity and the effective area of a magnetic field of the magnetic field generating unit 30 is adjusted, it may be identified that the electrons emitted by the radiation beam are moved along the irradiation direction of the radiation beam while being neither deflected nor dispersed to one area.

Accordingly, in the case of an organ (a lung, an oral cavity, or an airway) having a low density space therein, in order that electrons generated when a radiation beam is irradiated ae concentrated on a tumor that is a target without being neither deflected nor dispersed to an empty space area in the interior of the organ, a surface dose of a tumor may be enhanced and thus an effect of a radiotherapy may be improved by applying an magnetic field in a direction that is parallel to a beam locus of the radiation while charged particles, which are generated due to the heterogeneous density of the human body and the materials included in the beam locus of the radiation, are not dispersed but are concentrated on a surface of the tumor T so that divergence of the scattering charged particles when the charged particles travel to the surface of the tumor T that is a treatment target by adjusting the intensity and the effective area of the magnetic field of the magnetic field generating unit 30 through calculation of the calculation unit 50.

Figure 8:
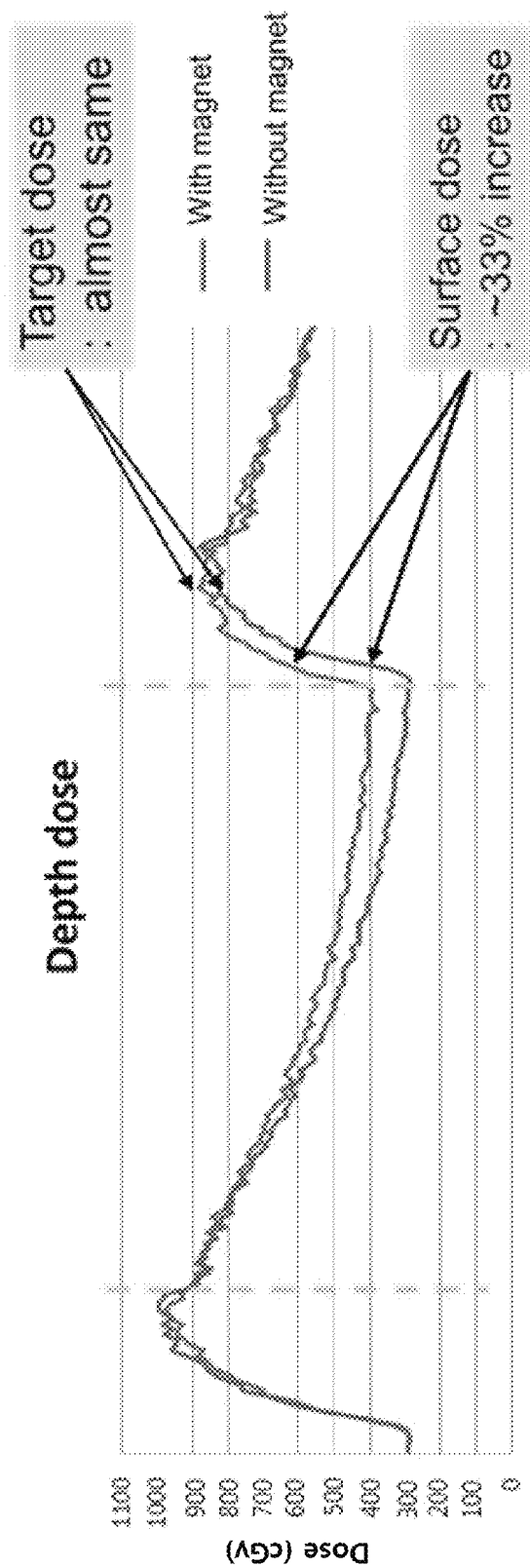
FIG. 8 is a graph illustrating a result that is obtained by measuring a radiation dose of a tumor by using the tumor surface dose enhancing radiotherapy apparatus using a magnetic field according to the inventive concept as an example.

FIG. 8 is a graph illustrating a result that is obtained by measuring a radiation dose of a tumor T by using the tumor surface dose enhancing radiotherapy apparatus using a magnetic field according to the inventive concept as an example.

FIG. 8 illustrates a result that is obtained by measuring a radiation dose depending on the irradiation depth of a radiation beam, when an X ray of 6 MV is irradiated to a tumor T on the right side from the radiation beam generating unit 20 situated on the left side via an organ of a diameter of 5 cm as illustrated in FIG. 6.

As illustrated in FIG. 8, it can be seen that a radiation dose on a surface of an organ situated on the front side of a tumor T, that is, a surface dose of a tumor increases by 33% as compared with the case in which a magnetic field is not formed in the interior of the human body.

Further, the radiation dose values at the tumor T that is a target may be different on a surface of an organ when a magnetic field area is not formed and when a magnetic field area is formed, but have similar values as the depth of the organ increases.

Accordingly, as illustrated in the test graph of FIG. 8, it may be identified that the tumor surface dose enhancing radiotherapy apparatus using a magnetic field according to the inventive concept improves a radiotherapy effect by enhancing a radiation dose that is delivered to a surface of a tumor T that is a target object and reduces a side effect of a radiation by decreasing damage to surrounding normal tissues due to additional use of radiation and divergence of scattering charged particles, when a radiation beam is irradiated after a magnetic field area is formed in the interior of the human body.

In this way, according to the inventive concept, the divergence of the scattering charged particles may be reduced and the surface dose of the target that is a treatment target may be increased by forming a magnetic field that is parallel to the direction of the beam of the radiation. That is, the additional irradiation of radiation beams for complementing for the lack of a dose on an adjacent surface of a tumor, which is caused when the scattering charged particles diverge at a portion having low density and the propagation of the radiation dose to the normal tissues, which is generated by the diverging charged particles can be solved, and a side effect of the radiation can be reduced and a treatment effect can be improved by securing a dose of a surface of the tumor.

Meanwhile, the radiation beam generating unit of the tumor surface dose enhancing radiotherapy apparatus using a magnetic field according to the inventive concept may include various types of medical radiation beam generating apparatuses that correspond to a linear accelerator that generates general MV X-rays, but also correspond to all radiation beams (electrons, protons, neutrons, baryons, and the like) that are charged particles themselves or are related to the charged particles In the case of a beam, such as an X ray, a gamma ray, or a neutron, which is not initially charged, a radiation dose is delivered mainly by secondarily charged particles, and concentration of the secondarily charged particles may be induced through formation of the magnetic field.

Further, the radiation beam generating unit of the tumor surface dose enhancing radiotherapy apparatus using a magnetic field according to the inventive concept may have a bore shape, a gantry shape, or a fixed shape.

Further, the magnetic field generating unit of the tumor surface dose enhancing radiotherapy apparatus using a magnetic field may be arranged to be integral with the radiation beam generating unit, to be independently movable, or to be fixed, and in this case, may have a structure that may change the direction of a magnetic field depending on the direction of the beam of the radiation. In the fixed magnetic field generating unit, a patient fixing table may be movable such that a radiation beam may be irradiated to a surface of a tumor that is a target object in various directions while the location of the patient is changed.

Further, the tumor surface dose enhancing radiotherapy apparatus using a magnetic field according to the inventive concept may be combined with a patient posture correcting apparatus using an image, and the information of the image may be used to optimize a magnetic field.

According to the inventive concept, divergence of scattering charged particles of a radiation beam can be prevented and scattering charged particles can be concentrated by forming a magnetic field that is parallel to a direction of a beam of radiation, whereby a radiotherapy effect can be improved by enhancing a radiation dose that is delivered to a surface of a tumor that is a target object and damage to surrounding normal tissues due to additional use of radiation beams and divergence of the scattering charged particles.

It is apparent to those skilled in the art to which the inventive concept pertains that the inventive concept is not limited to the above-mentioned embodiments, but may be variously corrected and modified without departing from the spirit and scope of the inventive concept. Accordingly, the corrections and modifications shall pertain to the scope of the claimed of the inventive concept.

What is claimed is:

1. A tumor surface dose enhancing radiotherapy apparatus using a magnetic field, comprising:
    a radiation beam generating unit that irradiates a radiation beam towards a tumor of a patient;
    a magnetic field generating unit that forms a magnetic field area that is parallel to the radiation beam between the radiation beam generating unit and the tumor of the patient; and
    a control unit that controls a surface dose of the tumor by adjusting an intensity and an effective area of the magnetic field area of the magnetic field generating unit,
    wherein the control unit further comprises a calculation unit that calculates the surface dose of the tumor that is delivered to the tumor of the patient via the magnetic field area.

2. The tumor surface dose enhancing radiotherapy apparatus of claim 1, wherein the magnetic field generating unit forms a homogenous or heterogeneous magnetic field area at a whole part or a portion of a beam locus of the radiation.

3. The tumor surface dose enhancing radiotherapy apparatus of claim 1, wherein the magnetic field generating unit comprises electromagnets, permanent magnets, or combination type magnets thereof.

4. The tumor surface dose enhancing radiotherapy apparatus of claim 1, wherein the magnetic field generating unit is rotated round the patient or is fixedly or movably arranged along a circumference of the patient.

* * * * *